United States Patent [19]

Sangekar et al.

[11] Patent Number: 5,000,962
[45] Date of Patent: Mar. 19, 1991

[54] LONG ACTING DILTIAZEM FORMULATION

[75] Inventors: Surendra Sangekar, Union; Winston A. Vadino, Whitehouse Station, both of N.J.; Eugenio A. Cefali, Plantation, Fla.

[73] Assignee: Schering Corporation, Kenilworth, N.J.

[21] Appl. No.: 398,209

[22] Filed: Aug. 25, 1989

[51] Int. Cl.$^5$ .............................................. A61K 9/32
[52] U.S. Cl. .................................. 424/482; 424/475; 424/480
[58] Field of Search ............... 424/499, 501, 475, 482, 424/468, 469, 470, 474, 480

[56] References Cited

U.S. PATENT DOCUMENTS

| | | | |
|---|---|---|---|
| 4,389,393 | 6/1983 | Schor et al. | 424/19 |
| 4,411,933 | 10/1983 | Samejima et al. | 427/213 |
| 4,443,497 | 4/1984 | Samejima et al. | 427/213 |
| 4,462,982 | 7/1984 | Samejima et al. | 424/35 |
| 4,542,042 | 9/1985 | Samejima et al. | 427/213 |
| 4,721,619 | 1/1988 | Panoz et al. | 424/459 |
| 4,784,858 | 11/1988 | Ventouras | 424/469 |
| 4,804,540 | 2/1989 | Nugent et al. | 424/469 |

FOREIGN PATENT DOCUMENTS

| | | |
|---|---|---|
| 898819 | 5/1984 | Belgium . |
| 900817 | 2/1985 | Belgium . |
| 900824 | 2/1985 | Belgium . |
| 901359 | 4/1985 | Belgium . |
| 903540 | 2/1986 | Belgium . |
| 315197 | 5/1989 | European Pat. Off. . |
| 59-010512 | 1/1984 | Japan . |
| 59-059632 | 4/1984 | Japan . |
| 59-065009 | 4/1984 | Japan . |
| 61-212517 | 9/1986 | Japan . |
| 62-005915 | 1/1987 | Japan . |

*Primary Examiner*—Thurman K. Page
*Attorney, Agent, or Firm*—Anita W. Magatti; James R. Nelson; Stephen I. Miller

[57] ABSTRACT

A long acting diltiazem formulation is disclosed that comprises more than 35 percent by weight of a swellable hydrophilic polymer.

Release rate is also controlled by the application of diffusion controlled membrane to the matrix tablet containing swellable hydrophilic polymers. The diffusion rate through the membrane depends upon the composition or ratio of hydrophilic to hydrophobic coating agent.

4 Claims, No Drawings

LONG ACTING DILTIAZEM FORMULATION

SUMMARY

The present invention encompasses long acting oral dosage forms and formulations for medicinal agents, and in particular for diltiazem.

One such oral dosage form is a long acting tablet, comprising an effective amount of active ingredient and excipients that may be compressed into a suitable oral dosage form, and which may be coated with one or more coating agents.

In a particular formulation described herein, a long acting tablet may contain diltiazem or a pharmaceutically acceptable salt thereof in combination with swellable hydrophilic polymers and other auxiliary excipients such as sugar, magnesium stearate and/or povidone.

BACKGROUND OF THE INVENTION

Numerous references disclosure diltiazem in sustained release formulations which utilize microencapsulation technology. For example are the following:

U.S. Pat. No. 4,452,042, issued to Samejima et al. on Sept. 17, 1985;

U.S. Pat. No. 4,462,982, issued to Samejima et al. on July 31, 1984;

U.S. Pat. No. 4,443,497, issued to Samejima et al. on Apr. 17, 1984; and

U.S. Pat. No. 4,411,933, issued to Samejima et al. on Oct. 25, 1983.

Similarly, numerous publications have disclosed devices which rely upon an osmotically regulated membrane for the controlled delivery of pharmaceuticals, such as diltiazem. For example are the following:

Belgian Application No. 900,817, published on Feb. 1, 1985 discloses a device comprising a semipermeable wall, an osmopolymer, such as poly(ethylene oxide) and an active ingredient.

Belgian Application No. 900,824 also published on Feb. 1, 1985 discloses a core and a membrane having variable permeability;

Belgian Application No. 898,819, published May 30, 1984, discloses a device for controlled drug delivery containing two compositions including poly(ethyleneoxide);

Belgian Application No. 903,540 published Feb. 17, 1986 discloses a sustained release powder, which can be formulated into an ointment, suspension etc.

Belgian Application No. 901,359 published Apr. 16, 1985 discloses a controlled release diltiazem formulation containing granules and a semipermeable external membrane.

Japanese Application No. 175,144 published on Apr. 13, 1984, discloses a sustained release thermoset or thermoplastic resin;

Japanese Application No. 170,440 published on Apr. 5, 1984, discloses a sustained release tablet which utilizes hardened oil;

Japanese Kokai No 62/5915, published Jan. 12, 1987, discloses diltiazem in combination with an acrylic acid resin;

Japanese Kokai No. 61/21517, published Sept. 20, 1986 discloses the use of diltiazem in combination with hydrogenated oils;

Japanese Kokai No. 59/10512 published Jan. 20, 1984, discloses microencapsulation of diltiazem, which is coated with ethylcellulose;

Panoz and Geohagan, U.S. Pat. No. 4,721,619 discloses an alternating arrangement (between 50 and 200 layers) of diltiazem, organic acid and lubricant layers and polymeric material layers built upon a central inert core.

Schor et al., U.S. Pat. No. 4,389,393 discloses a sustained release tablet which is one or more hydroxypropylmethylcellulose or a mixture of one or more hydroxypropylmethylcelluloses and up to 30% by weight of the mixture of methylcellulose, sodium carboxymethylcellulose and/or other cellulose ether, and wherein at least one of the hydroxypropylmethylcelluloses has a methoxy content of 16–24 weight-%, a hydroxypropyl content of 4–32 weight-% and a number average molecular weight of at least 50,000 and wherein the carrier base material constitutes less than about one third of the weight of the solid unit dosage form.

However, none of the references disclose a long acting release diltiazem tablet formulation utilizing a uniformly dispersed hydrophilic matrix containing more than about 30 percent by weight of HPMC.

DETAILED DESCRIPTION

The present invention relates to a novel long acting tablet, useful in that it exhibits unexpectedly prolonged activity over an extended period of time. The long acting diltiazem tablets described herein will be suitable for once a day and twice daily administration.

A preferred long acting tablet falling within the scope of the invention utilizes diltiazem hydrochloride or a solvate thereof as the active ingredient. Preferably the amount of the active ingredient, such as diltiazem, will be present at about 20 to 500 mg per tablet (3 to 80 percent by weight), more preferably at about 30 to 360 mg per tablet (3 to 57 percent by weight) and most preferably at about 90 to 240 mg per tablet (14 to 38 percent by weight).

The diltiazem utilized herein also encompasses other pharmaceutically acceptable acid addition salt forms thereof, as well as other pharmaceutically acceptable salts and esters thereof, e.g., diltiazem tartarate. As described above, the diltiazem used in Examples 1 to 3 below is the hydrochloride salt. Also included herein are stereospecific salt forms of diltiazem, both in pure form and racemic mixture. One such example is the (d,l) lactate form of diltiazem.

The tablets of the invention utilize a swellable hydrophilic polymer, into which the active ingredient is incorporated. The tablets also include other auxiliary excipients. These dosage forms slowly hydrate as they come in contact with gastric fluid or aqueous media and slowly release the active ingredient by diffusion and/or erosion of the swollen matrix layer.

Examples of swellable hydrophilic polymers include: hydroxypropylmethyl cellulose; hydroxypropylcellulose; methylcellulose; hydroxymethylcellulose; hydroxyethylcellulose; hydroxypropylcellulose, which can be used alone or in combination; carboxymethyl cellulose and the sodium salt thereof, which can be used alone or in combination; and other hydrocolloids, such as acacia and guar gum. The preferred swellable hydrophilic polymer is either hydroxypropylmethylcellulose or hydroxypropylcellulose.

The swellable hydrophilic polymers comprise from about 35 to about 60 percent by weight of the core.

Preferably, the swellable hydrophilic polymers comprise from about 35 to about 45 percent by weight of the core and most preferably they comprise about 40 percent by weight of the core.

The hydroxypropylmethylcelluloses (HPMC) utilized in the present invention are water soluble cellulose ethers, and include, but are not limited to, USP 2208USP 2906 and USP 2910. Examples of such materials are commercially available from Dow Chemical Co. in various grades under several tradenames, including METHOCEL E, (USP 2910), METHOCEL F, (USP 2906) and METHOCEL K, (USP 2208). The various grades differ in methoxy and hydroxypropoxyl content as well as molecular weight and viscosity. Preferred hydroxypropylmethylcellulose polymers useful in carrying out the invention include METHOCEL E4M, characterized by having a 28–30 weight percent methoxyl content, a 7–12 weight percent hydroxypropoxyl content, and a number average molecular weight of 93,000 and a viscosity in a 2% aqueous solution of 3500–5600 cps (centipoises per second); and METHOCEL K100 having a 19–24 weight percent methoxyl content, a 7–12 weight percent hydroxypropoxyl content, and a number average molecular weight of 246,000, and a viscosity in a 2% aqueous solution of 100,000 cps; and METHOCEL F4M having a 26–30 weight (number average molecular weights of 85000–115000) percent methoxy content, a 4–6 percent hydroxypropoxyl content, and a number average molecular weight of 86,000, and a viscosity in a 2% aqueous solution of 3500–5600 cps.

The hydroxypropylcellulose utilized in the present invention is a high viscosity nonionic water soluble cellulose ether. These are commercially available, e.g. Klucel HXF manufactured by Aqualon Company, which is a member of the Aqualon Group of Wilmington, Del., is a fine particle size hydroxypropylcellulose with a viscosity of a 1 percent aqueous solution of 1,500 to 3,000 cps.

Examples of auxiliary excipients utilized in the present invention include: diluents, binders and lubricants. The diluent may constitute from about 10 to about 50 percent by weight of the core but will preferably constitute from about 14 to about 38 percent by weight of the core. The diluent can be a sugar, e.g., mannitol or lactose, and lactose is preferred. Such lactose can be used in the direct tabletting grade as available from Shefield Corp. of Norwick, N.Y., and alternately it can be used in the hydrous form or as spray dried lactose.

The binder used in the present invention comprises a polymeric binder that combines with the swellable hydrophilic polymer, and therefore includes low viscosity hydroxypropylmethylcellulose, low viscosity hydroxypropylcellulose, carboxymethylcellulose and ethylcellulose, as described above. The preferred is polyvinylpyrrolidone (povidone). the binder comprises from about 2 to about 6 percent by weight of the tablet, preferably about 4 percent by weight of the tablet.

The polyvinylpyrrolidone utilized in the present invention is a synthetic polymer consisting of linear 1-vinyl-2-pyrrolidinone groups in which the degree of polymerization results in polymers of various molecular weights. It is characterized by its viscosity in aqueous solution, relative to that of water, expresses as a K-value, ranging from 10 to 95. An example of a polyvinylpyrrolidinone useful in the formation of this invention is Povidone USP K29/32 having an average molecular weight of about 40,000 supplied by GAF Corp., Wayne, N.J.

Examples of lubricants utilized in the present invention include magnesium stearate, calcium stearate, stearic acid and the like, with the preferred lubricant being magnesium stearate. The lubricant comprises from about 0.5 to about 3 percent by weight of the tablet, preferably about 1 to about 3 percent by weight and most preferably about 1.5 percent by weight of the tablet. The lubricants are commercially available, e.g. magnesium stearate NF is commercially available from Mallinckrodt Inc., St. Louis, Mo.

To further modify the release rates, the swellable hydrophilic matrix cores can be coated with a diffusion controlled membrane comprising a mixture of hydrophobic and or hydrophilic film forming agents in combination with plasticizers. In vitro release rates of tablets included in this aspect of the invention depend upon the composition and concentration of polymer used in the swellable hydrophilic core as well as the type, amount and ratio of hydrophobic to hydrophilic film forming polymers used in the coating part of the system.

Examples of film forming agents include an aqueous dispersion of ethylcellulose (available from Colorcon Inc., West Point, Pa. 19486, under the tradename of Surelease ®) and/or low viscosity hydroxypropylcellulose (available from Colorcon Inc., West Point, Pa. 19486, under the tradename of Opadry ® clear which, in addition to, low viscosity hydroxypropylcellulose contains plasticizers). In addition to the above, several other hydrophilic and hydrophobic polymers can be used to give a diffusion controlled release membrane, e.g., polyvinylpyrrolidone of various molecular weights available from GAF Corp. Wayne, N.J., low viscosity hydroxypropylcellulose available from Aqualon Company, which is a member of the Aqualon Group of Wilmington, Del., polyvinyl alcohol and its ester available from American Hoechst Corp., Speciality Products Group, Sommerville, N.J., Alginic acid and its salts, available from Kelco, P.O. Box 23076San Diego, Calif.

Examples of plasticizers include, but are not limited to, diethyl phthalate, and triacetin available from Eastman Chemical Products Inc., P.O. Box 431Kingsport, Tenn. 37662. Dibutyl sebacate available from Eastman Kodak Company, Rochester, N.Y. 14650, polyethylene glycols available from Union Carbide, Danbury, Conn., 06817.

The film forming agent comprises 3 to 10 percent of the tablet, preferably 4.5 to 8.5 percent, most preferably 5 to 6.5%.

Ratios of hydrophobic to hydrophilic polymers can range from 5:1 to 1:1, preferably 4:1 to 1:1, most preferably 3:1 to 1:1.

In preparing the tablest of the invention, conventional tabletting techniques are employed, for example dry granulation or wet granulation, and direct compression. One method for manufacturing the tablets involves blending the diltiazem hydrochloride, the diluents, and the hydrophilic binder, then granulating the mixture with a solution of binder in water or alcohol or the mixture thereof. The granules can then be dried and milled if necessary. Any other ingredients such as lubricants (e.g., magnesium stearate) and the like are added to the granules, mixed and compressed into a suitable size and shape using conventional tabletting machines such as a rotary tablet press. These tablets may then be used as is or they can be film or sugar coated or coated with controlled release coating techniques that are well known in the art.

The following examples describe typical tablet formulations and dissolution profiles of the long acting dosage forms of the present invention, but they are not to be interpreted as limiting the scope of the appended claims in any way.

EXAMPLE 1

Tablets with Hydroxypropylmethylcellulose and Povidone as Binder

The following tablets were prepared as described in the preparation above and release rates were determined using the USP paddle method (as described in USPxxi) at 50 revolutions per minute (RPM) in 1000 ml of purified water.

TABLET PREPARATION

| Composition | Batch 1 (mg/tablet) | Batch 2 (mg/tablet) |
|---|---|---|
| Diltiazem HCl | 180 | 90 |
| Lactose NF | 165 | 255 |
| Hydroxypropylmethylcellulose USP 2910 (Methocel E4M) | 250 | 250 |
| Povidone USP (K 29/32) | 25 | 25 |
| Magnesium Stearate NF | 10 | 10 |
| TOTAL | 630 | 630 |

RELEASE RATES

| | Percent Dissolution | |
|---|---|---|
| Time in Hours | Batch 1 | Batch 2 |
| 1 | 20 | 19 |
| 2 | 31 | 30 |
| 4 | 48 | 46 |
| 6 | 62 | 59 |
| 8 | 73 | 69 |
| 12 | 87 | 83 |
| 16 | 93 | 90 |
| 20 | 95 | — |

EXAMPLE 2

Tablets with Hydroxypropylmethylcellulose and Ethyl Cellulose as Binder

The following tablets were prepared as described in the preparation above and release rates were determined using the USP paddle method (described in USPxxi) at 100 RPM in 1000 ml of purified water.

TABLET PREPARATION

| Composition | Batch 3 (mg/tablet) |
|---|---|
| Diltiazem HCl | 90 |
| Lactose NF | 255 |
| Hydroxypropylmethyl cellulose USP 2208 (Methocel K100M) | 250 |
| Ethylcellulose NF (type 7) | 25 |
| Magnesium Stearate NF | 10 |
| TOTAL | 630 |

RELEASE RATES

| | Percent Dissolution |
|---|---|
| Time in Hours | Batch 3 |
| 1 | 20 |
| 2 | 30 |
| 4 | 44 |
| 6 | 55 |
| 8 | 64 |
| 12 | 76 |
| 16 | 83 |
| 20 | 86 |

EXAMPLE 3

Tablets with Hydroxypropylcellulose and Povidone or Ethyl Cellulose as binders

The following tablets were prepared as described in the preparation above and release rates were determined using the USP paddle method (described in USP xxi) at 100 RPM in 1000 ml of purified water.

TABLET PREPARATION

| Composition | Batch 4 (mg/tablet) | Batch 5 (mg/tablet) |
|---|---|---|
| Diltiazem HCl | 90 | 90 |
| Lactose NF | 255 | 255 |
| Hydroxypropylcellulose USP (Klucel HXF) | 250 | 250 |
| Povidone USP (K 29/32) | 25 | 0 |
| Ethylcellulose NF Type 7 | 0 | 25 |
| Magnesium Stearate NF | 10 | 10 |
| TOTAL | 630 | 630 |

RELEASE RATES

| | Percent Dissolution | |
|---|---|---|
| Time in Hours | Batch 4 | Batch 5 |
| 1 | 21 | 23 |
| 2 | 32 | 33 |
| 4 | 46 | 48 |
| 6 | 57 | 58 |
| 8 | 66 | 66 |
| 12 | 78 | 78 |
| 16 | 86 | 86 |
| 20 | 89 | 90 |

EXAMPLE 4

Tablets with Hydroxypropylmethylcellulose and Povidone as Binders and Coating

The following tablets were prepared as described in the preparation above and release rates were determined using the USP paddle method (described in USP xxi) at 100 RPM in 1000 ml of purified water.

| Composition Core | Batch 6 | Batch 7 | Batch 8 | Batch 9 |
|---|---|---|---|---|
| Diltiazem HCl | 180 | 180 | 180 | 180 |
| Lactose NF | 165 | 165 | 165 | 165 |
| Hydroxypropylmethylcellulose USP 2208 (Methocel K100M) | 250 | 250 | 250 | 250 |
| Povidone USP (K29/32) | 25 | 25 | 25 | 25 |
| Magnesium Stearate NF | 10 | 10 | 10 | 10 |
| Coat | | | | |
| Surelease ® (solids) | — | 40 | 23.6 | 28.8 |
| Opadry ® | — | — | 16.4 | 11.2 |
| Approximate Weight | 630 | 670 | 670 | 670 |

RELEASE RATES

| | Percent Dissolution | | | |
|---|---|---|---|---|
| Time (hrs) | BATCH 5 | BATCH 7 | BATCH 8 | BATCH 9 |
| 1 | 20 | 0 | 13 | 7 |
| 2 | 31 | 0 | 24 | 17 |
| 4 | 48 | 1 | 41 | 33 |
| 6 | 62 | 0 | 55 | 47 |
| 8 | 73 | 1 | 66 | 59 |
| 12 | 87 | 3 | 81 | 77 |

| | -continued | | | |
|---|---|---|---|---|
| 16 | 93 | 8 | 89 | 88 |
| 20 | 95 | 16 | 91 | 92 |

EXAMPLE 5

Tablets with Hydroxypropylcellulose and Povidone as binders and Coating

The following tablets were prepared as described in the preparation above and release rates were determined using the USP paddle method (described in USP xxi) at 100 RPM in 1000 ml of purified water.

| Composition Core | Batch 10 (mg/tablet) | Batch 11 (mg/tablet) |
|---|---|---|
| Diltiazem HCl | 90 | 90 |
| Lactose NF | 255 | 255 |
| Hydroxypropylcellulose (Klucel HXF) | 250 | 250 |
| Povidone USP (K29/32) | 25 | 25 |
| Magnesium Stearate NF | 10 | 10 |
| Coat | | |
| Surelease ® (solids) | — | 28.8 |
| Opadry ® | — | 11.2 |
| Approximate Weight | 630 | 670 |

| RELEASE RATES | | |
|---|---|---|
| | Percent Dissolution | |
| Time (hrs) | Batch 10 | Batch 11 |
| 1 | 24 | 5 |
| 2 | 36 | 12 |
| 4 | 52 | 25 |
| 6 | 64 | 35 |
| 8 | 73 | 43 |
| 12 | 85 | 58 |
| 16 | 91 | 69 |
| 20 | 93 | 76 |

We claim:
1. A long acting diltiazem tablet consisting essentially of:
   (a) 3 to 80 percent diltiazem hydrochloride;
   (b) 35 to 60 percent hydroxypropylmethyl cellulose;
   (c) 2 to 6 percent polyvinylpyrrolidone;
   (d) 0.5 to 3 percent magnesium stearate; and
   (e) 10 to 50 percent lactose.
2. The long acting diltiazem tablet defined in claim 1 consisting essentially of
   (a) 3 to 57 percent diltiazem hydrochloride;
   (b) 35 to 45 percent hydroxypropylmethyl cellulose;
   (c) 2 to 6 percent polyvinylpyrrolidone;
   (d) 1 to 3 percent magnesium stearate; and
   (e) 14 to 38 percent lactose.
3. The long acting diltiazem tablet defined in claim 2 consisting essentially of
   (a) 14 to 38 percent diltiazem hydrochloride;
   (b) 35 to 45 percent hydroxypropylmethyl cellulose;
   (c) about 4 percent polyvinylpyrrolidone,
   (d) 1 to 2 percent magnesium stearate; and
   (e) 14 to 38 percent lactose.
4. A long acting diltiazem coated tablet wherein the tablet core consists essentially of:
   diltiazem or a pharmaceutically acceptable salt thereof in an amount of from 3 to 80 percent by weight;
   a swellable hydrophilic polymer in an amount of at least 35 percent by weight;
   a binder in an amount of 2 to 6 percent by weight;
   a lubricant in an amount of 0.5 to 3 percent by weight; and
   a diluent in an amount of 10 to 50 percent by weight;
   and wherein the coating comprises film forming agents in combination with plasticizers.

* * * * *